(12) United States Patent
Makosky et al.

(10) Patent No.: US 8,790,354 B2
(45) Date of Patent: Jul. 29, 2014

(54) INSECT LOCATOR AND REMOVAL TOOL

(75) Inventors: Frank J. Makosky, Stroudsburg, PA (US); Debra Galan-Parsons, Kunkletown, PA (US)

(73) Assignee: Sangria Enterprises, LLC, Stroudsberg, PA (US)

( * ) Notice: Subject to any disclaimer, the term of this patent is extended or adjusted under 35 U.S.C. 154(b) by 0 days.

(21) Appl. No.: 13/506,973

(22) Filed: May 29, 2012

(65) Prior Publication Data
US 2013/0324802 A1    Dec. 5, 2013

(51) Int. Cl.
*A61B 17/50* (2006.01)
(52) U.S. Cl.
USPC .......................... 606/131; 359/802; 359/803
(58) Field of Classification Search
USPC ............... 600/101–183, 184–246, 247–248;
359/802–803; 132/219, 101–163;
119/611–617, 655, 664; 606/131
See application file for complete search history.

(56) References Cited

U.S. PATENT DOCUMENTS

| | | | | |
|---|---|---|---|---|
| 4,836,596 A | * | 6/1989 | Owen | 294/99.2 |
| 5,618,289 A | * | 4/1997 | Aragona et al. | 606/131 |
| 7,339,754 B2 | * | 3/2008 | Neal et al. | 359/802 |
| D572,334 S | * | 7/2008 | Pabari et al. | D22/122 |

* cited by examiner

*Primary Examiner* — Pedro Philogene
*Assistant Examiner* — Christina Negrellirodrigue
(74) *Attorney, Agent, or Firm* — Armand M. Vozzo, Jr.

(57) ABSTRACT

A hand-held tool for locating and removing parasitic insects from hair-covered skin comprises a tool body including a pad-like head portion with extended handle and a magnifying window incorporated therein; a linear set of rake-like teeth along one side of the window projecting at a 90° thereto; and a separate set of comb-like teeth along the opposite side of the window projecting at about 45°. With means for illuminating the viewing area further provided around the magnifying window, the tool is stroked through the hair with the rake-like teeth passing in the direction opposite from the natural growth of the hair to provide an illuminated and magnified view of exposed skin area through the window as the hair is pulled back by the rake-like teeth. If an insect is viewed, the tool is stroked in reverse through the same area leading with the comb-like teeth to collect and remove the insect.

13 Claims, 5 Drawing Sheets

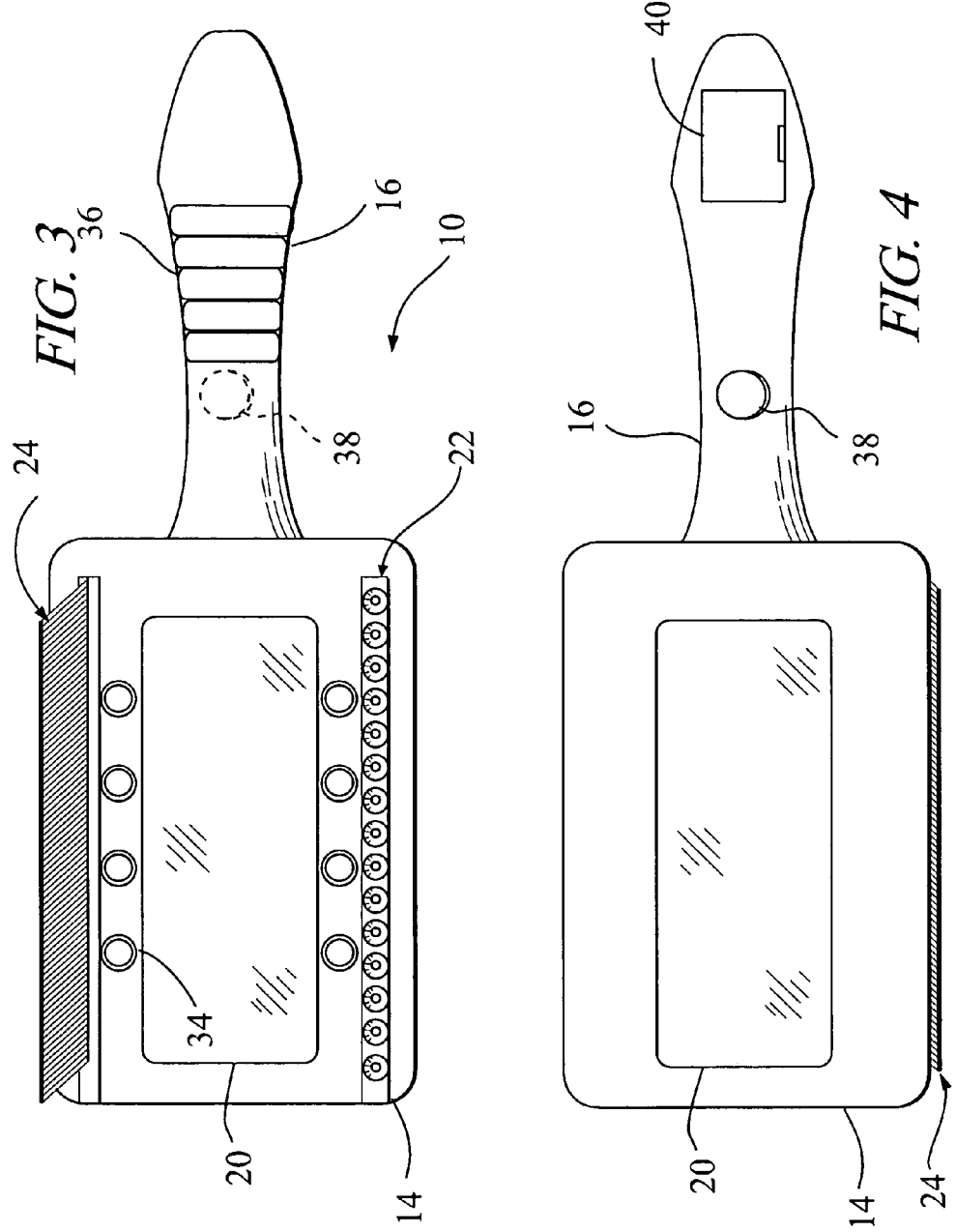

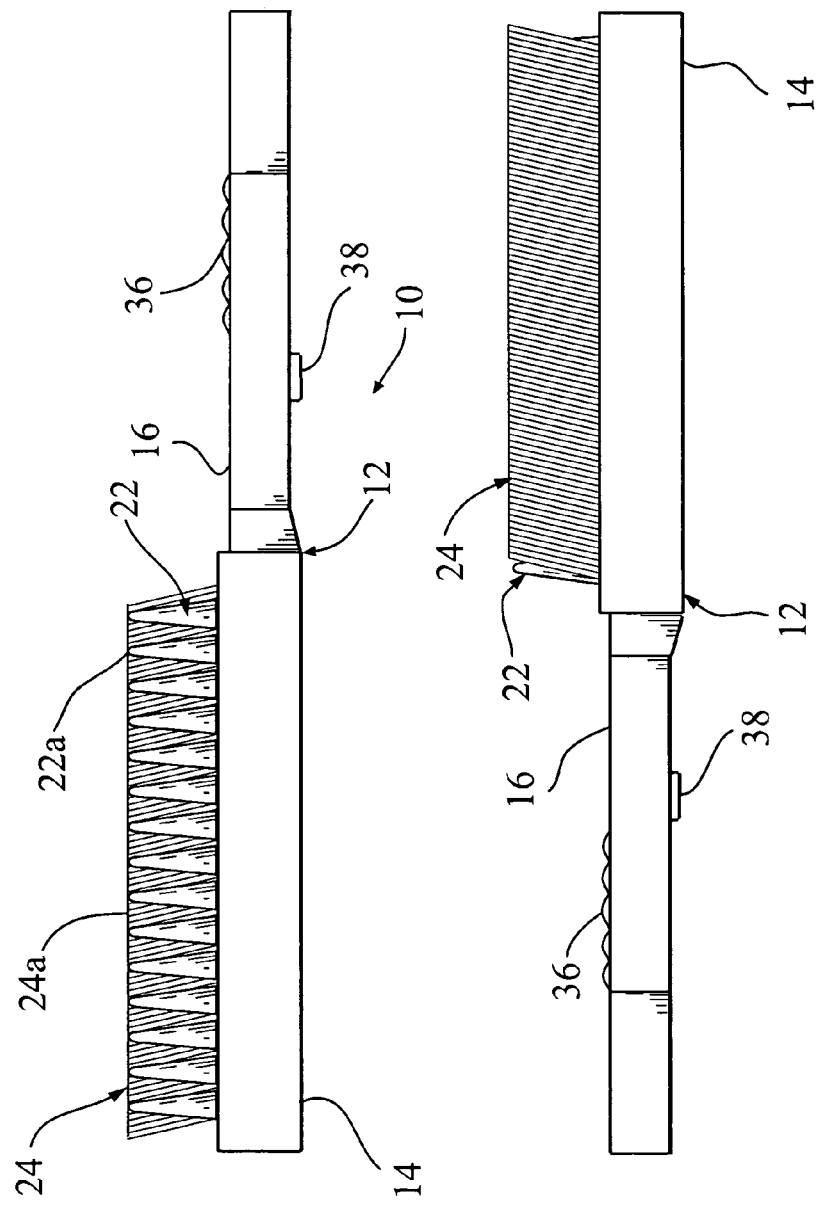

INSECT LOCATOR AND REMOVAL TOOL

BACKGROUND OF THE INVENTION

The present invention relates generally to appliances used for removing certain parasitic insects, like lice, ticks and fleas, from the skin of humans and pets, and more particularly to a single hand-held tool for finding parasitic insects upon sections of hair-covered skin and removing the insects as they are found in a systematic process using the single tool.

Ectoparasites are parasitic insects that live in or on the skin of a host, and an associated infestation can cause significant harm to the affected host, be it human or animal, by way of infections and the transmittal of disease that the insects carry. Such parasitic insects include lice, bedbugs, fleas and ticks, all of which can carry harmful pathogens that may infect the host and cause a variety of diseases. Ticks, for example, can be vectors of many harmful diseases, including Lyme disease, Anaplasmosis, Ehrlichia and Rocky Mountain spotted fever, and the human victims of any of these diseases can further develop secondary, sometimes more serious conditions such as renal disease. Fleas are more troublesome to pet animals, but besides causing discomfort to the pet and an infestation of the home, a flea infestation can induce allergic dermatitis that is costly for the pet owner to treat and may also lead to a tapeworm infestation of the animal. While flea treatments and other preventatives can be effective, they can prove to be very costly and in some cases, contain harmful insecticides.

Good grooming and regular cleaning can help to reduce the likelihood of an infestation by these parasitic insects. However, there is little that can be done to eradicate these ecto-parasites and prevent an infestation from occurring as long as the potential host, pet or human, is outdoors and exposed to wildlife or an environment wherein these parasitic insects thrive. Careful inspection of the skin surfaces, therefore, is most important after coming in from out of doors or whenever there is a suspected exposure to any one of these parasitic insects. Unfortunately, these insects, particularly the so-called deer ticks, are extremely small and thus hard to locate, the nymph stage of these deer ticks being approximately one half millimeter in size. Compounding the problem of size in the detection process is the fact that the skin of the host is typically hair-covered, whether human or animal, so that location of the insects, often embedded in the skin, can be very difficult and time-consuming as it is typically required under the cover of human hair, such as in the area of the human scalp, or on the hair-coated body of a dog or cat. Once an ectoparasite is detected, its removal from the skin is always necessary to prevent disease transmittal. This entire process of location and removal of the parasitic insect is generally difficult, and even more so when involving children, long-haired individuals or restless pets.

Prior art forms of tools and appliances have been devised and developed, some to aid the process of locating the parasitic insects and others to facilitate and effect their removal from the host victim. A recent example of the former type of parasitic insect locator is shown and described in U.S. Pat. No. 5,618,289 to Aragonna et al., while a more recent example of the latter type of insect removal device is shown and described in U.S. Pat. No. 6,100,501 to von der Hyde. While these and other prior art devices have been satisfactory and appear effective in either locating the parasitic insect on the hair-covered host or in facilitating the removal of the insect, they have been limited in their respective functions and not able to effectively serve both functions of insect location and removal that is required to fully and safely treat the affected host victim of an ectoparasite infestation. Accordingly, there is a need for an improved hand-held tool for both locating parasitic insects upon sections of hair-covered skin and then removing the insects as they are located in a systematic process using the single tool.

SUMMARY OF THE INVENTION

Accordingly, it is a general purpose and object of the present invention to provide an improved tool for both locating and removing parasitic insects, such as fleas, lice and ticks, and other foreign matter from the hair-covered skin of the host victim.

A more particular object of the present invention is to provide a single hand-held tool capable of locating parasitic insects and other foreign matter upon areas of hair-covered skin and of further removing the insects and other located matter in a systematic process using the single tool.

Another object of the present invention is to provide an improved insect locator and removal tool that is easy to manipulate and safe to use on the hair-covered skin of pet animals and humans.

Still another object of the present invention is to provide an improved insect locator and removal tool that is adaptable for use upon a variety of hair-covered surfaces and easily cleaned for repeated usage.

A still further object of the present invention is to provide an insect locator and removal tool that is lightweight and portable, relatively inexpensive to fabricate and simple to assemble.

Briefly, these and other objects of the present invention are accomplished by an improved hand-held tool for locating and removing parasitic insects from beneath hair-covered skin. The insect locator and removal tool comprises a tool body including a pad-like head portion with extended handle and a magnifying window incorporated into the head portion; a linear set of rake-like teeth disposed along one side of the window and projecting at a 90° angle thereto; and a finer set of comb-like teeth disposed along the opposite side of the window projecting at about 45°, both sets of teeth being removable in assemblies from the head portion for cleaning and replacement. Means for illuminating the viewing area around the magnifying window are further provided and include a series of LED lights stationed on the head portion and linked to a DC battery or other power source in the handle. With the illumination turned on and the separate sets of teeth turned away from the user, the tool is stroked gently through the hair of the pet with the rake-like teeth passing in the direction opposite from the natural growth of the hair to provide a clear and magnified view of exposed skin area through the window as the hair is pulled back by the rake-like teeth. If an insect is located, the user simply reverses the stroke through the exposed area leading with the comb-like teeth to gently remove the insect.

For a better understanding of these and other aspects of the present invention, reference should be made to the following detailed description taken in conjunction with the accompanying drawings in which like reference numerals and character designate like parts throughout the figures thereof.

BRIEF DESCRIPTION OF THE DRAWINGS

For a fuller understanding of the nature and objects of the present invention, references in the detailed description set forth below shall be made to the accompanying drawings in which:

FIG. 3 is a plan view of the working side of the insect locator and removal tool of FIG. 1;

FIG. 4 is a plan view of the present insect locator and removal tool from the opposite or viewing side of the tool shown in FIG. 3;

FIG. 5 is a longitudinal elevation of the insect locator and removal tool of FIG. 1 viewed from alongside of the set of rake-like teeth;

FIG. 6 is a longitudinal elevation of the insect locator and removal tool similar to that of FIG. 5 but from the opposite side alongside the set of fine comb-like teeth;

DETAILED DESCRIPTION OF THE INVENTION

Figure 1:
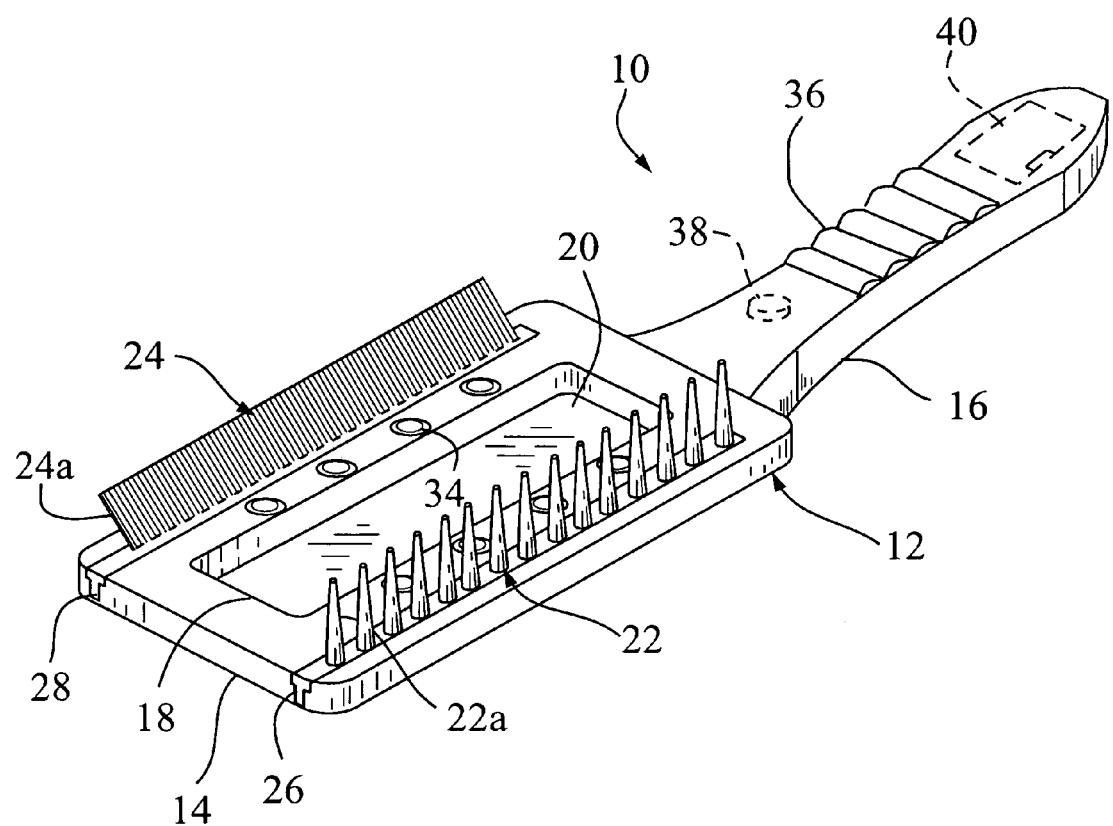
FIG. 1 is a perspective view from above the working side of a preferred embodiment of the present insect locator and removal tool shown with respective sets of teeth elements disposed in place.

The following is a detailed description of a preferred and alternate embodiment of the present invention and the best presently contemplated mode of their production and practice. This description is further made for the purpose of illustrating the general principles of the invention but should not be taken in a limiting sense, the scope of the invention being best determined by reference to appended claims.

Referring to the drawings, the following is a list of structural components of the present insect locator and removal tool, generally designated 10, and those associated structural elements shown employed in connection with the present invention:

10 insect locator and removal tool;
12 tool body;
14 tool head;
16 tool handle;
18 tool head opening;
20 magnifying window;
22 rake-like teeth set;
22a rake-like teeth members;
24 comb-like teeth set;
24a tine members;
26 base strip for rake-like teeth;
28 base strip for comb-like teeth;
30 mounting slot for rake-like teeth set;
32 mounting slot for comb-like teeth set;
34 light-emitting elements;
36 gripping elements;
38 switch device;
40 compartment cover;
42 DC battery;
44 electrical switch;
46 electrical resistors:
50 alternate tool embodiment;
52 alternate tool body;
54 alternate tool head:
56 alternate tool handle
58 alternate tool head opening;
60 magnifying window;
62 rake-like teeth set;
62a rake-like teeth members;
64 comb-like teeth set;
64a tine members;
66 base strip for rake-like teeth;
68 base strip for comb-like teeth;
70 mounting slot for rake-like teeth set;
72 mounting slot for comb-like teeth set;
74 light-emitting elements;
76 gripping elements; and
78 switch device.

Referring initially to FIG. 1, the present insect locator and removal tool 10 is a hand-held instrument somewhat resembling a flat or "paddle" hair brush in its basic configuration, the present tool being formed having a longitudinal body 12 with a pad-like head portion 14 and a handle portion 16 attached at one end of the head portion and made to extend therefrom in substantially the same plane. The head portion 14 is substantially rectangular in its perimeter outline, while the handle 16 is about the same length as the head portion but made narrower in width dimension and preferably contoured along its length for gripping purposes. The head portion 14 and handle portion 16 of the tool body 12 are constructed of a strong and durable material, such as a molded plastic, with both portions being formed having substantially the same exterior height dimension, better seen in FIGS. 5 and 6. The head portion 14 and handle 16 are preferably formed having interior chambers within each, the chamber of the handle extending longitudinally therethrough and connecting with that of the interior chamber of the head portion to permit mounting of electrical elements and routing of electrical connections within the tool body 12 that are associated with the illumination feature of the present inventive tool 10 described below in greater detail.

In accordance with the present invention, the head portion 14 of the tool body 12 is further formed and fabricated having a central opening 18 made through the thickness or height dimension of the head portion to provide visibility therethrough. The central opening 18 is substantially rectangular in its configuration and is sized to maximize the field of view observed through the head portion 14, the opening extending longitudinally within the head portion the greater part of its length. A magnifying lens element 20 made of an optical glass or acrylic material is made to insert and mount in place within the opening 18, with the lens element preferably being formed and adapted to press into engagement within the central opening and be similarly disengaged therefrom for replacement and cleaning as needed. The magnifying lens element 20 may alternatively be removably mounted within the central opening 18, for example, by a longitudinal insertion of the separate lens element from the outside end of the head portion 14 and effected through a slot or channel formed therein to provide access to the central opening. The magnifying lens element 20 may also be fixed in place within the central opening 18 to provide the intended magnifying window, the perimeter of the lens element being attached to the surrounding surface of the head portion 14. Because of the minute size of the flea and tick bodies, particularly those in the nymph stage, that are being targeted with the present insect locator and removal tool 10, the magnification power of the magnifying lens element 20 should be at least 4× to make those insect bodies sufficiently visible to the user through the magnifying window, with the preferred magnification power being in the range between 10×-30×.

Figure 2:
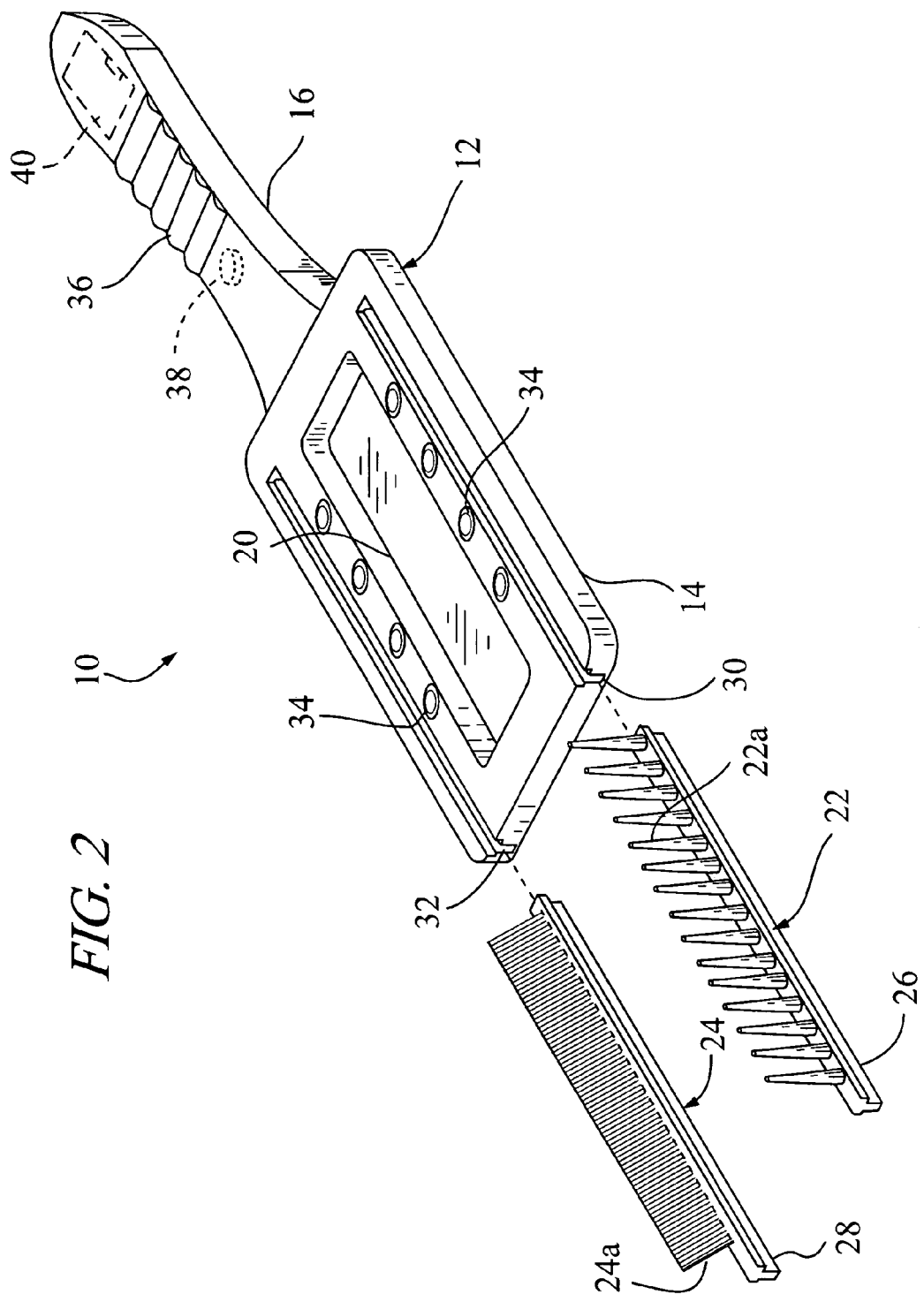
FIG. 2 is a similar perspective view of the insect locator and removal tool of FIG. 1 but shown with assemblies of the respective sets of teeth elements separated from the working side of the tool.

Referring now to FIG. 2 in conjunction with FIG. 1, the present insect locator and removal tool 10 further comprises separate assemblies of a rake-like teeth set 22 and a comb-like teeth set 24, both assembled sets being disposed on the working side of the tool with the respective sets being disposed longitudinally along the head portion 14 on opposite sides of the magnifying window of lens element 20.

The rake-like assembly set 22 includes a plurality of relatively firm but still flexible teeth members 22a that are assembled together in a linear series and mounted along a base strip 26 having a T-shaped configuration. The rake-like teeth members 22a are relatively thick compared to those of the comb-like teeth set 24 and are spaced apart and aligned in parallel along the top of the base strip 26 so that the assembled rake-like set 22 may project at a substantially 90° angle to the surface of the head portion 14 when the base strip is mounted thereon in its proper location. A mounting slot 30 formed within the head portion 14 and extending substantially along the length thereof is made to conform to the configuration of the base strip 26 so that the length of the base strip may be engaged within the slot and held within the head portion with the associated rake-like set of teeth 22 projecting therefrom at the 90° angle. The form and spacing arrangement of the rake-like teeth members 22a are designed to engage the hair of a human or animal and together are intended for parting, untangling and/or uncurling the hair, when necessary, so that an area or region of the skin beneath the hair may be exposed upon moving the rake-like assembly set 22 through the hair. The rake-like teeth members 22a are preferably made of a plastic material and have blunted or rounded tips to avoid scratching or abrading the scalp or skin surface of the treated human or animal when the rake-like set 22 makes contact with the surface as it moves through the hair.

The comb-like teeth set 24 comprises a plurality of relatively stiff teeth members or tines 24a that are very fine and narrow in form and closely spaced apart in a linear series. The tine members 24a are mounted together along a base strip 28 having a T-shaped configuration similar to that of base strip 26. The tine members 24a are closely set and aligned in parallel and mounted together along the top of the base strip 28 so that the assembled comb-like set 24 may project at an inclined angle, most suitably determined to be about 45°, to the surface of the head portion 14 when the base strip is mounted thereon in its proper location. A mounting slot 32 formed within the head portion 14 in similar fashion to slot 30 but on the opposite side of the magnifying lens element 20 is made to conform to the configuration of the base strip 28 so that the length of the base strip may be engaged within the associated slot and held within the head portion with the associated comb-like set 24 projecting outwardly and away from the magnifying window at the inclined angle. The form and spacing arrangement of the tine members 24a are designed to engage, collect and remove any insects or associated debris that may be found in the exposed area or region of the skin beneath the hair after moving the rake-like assembly set 22 therethrough. The tine members 24a are preferably made from a treated metal, such stainless steel, and should be slightly rounded at their tips to avoid unnecessarily penetrating the scalp or skin surface of the treated human or animal while the comb-like set 24 is being manipulated and makes contact with the skin surface.

As best seen in FIG. 2, both the rake-like teeth set 22 and the comb-like set 24 are removable from the head portion 14 and their respective mounting slots 30 and 32 formed therein. Each of the base strips 26 and 28 are formed in their cross sections to fit into the slots 30 and 32 and slide longitudinally into place within the head portion 14 for the intended use of the present tool 10. When not in use, the separate teeth sets 22 and 24 may be removed by sliding their respective base strips 26 and 28 from the slots 30 and 32, disengaging the teeth sets from the head portion 14 so that they may be cleaned or replaced for further use. It should be noted and understood that this feature of releasable engagement of the assembled sets of rake-like and comb-like teeth 22 and 24, respectively, will support and permit use of alternate versions of those assembled sets of teeth having special size, form and spacing of the respective rake-like teeth members 22a and tines 24a determined to be more suitable for a particular hair-covered surface being treated.

Referring further to FIGS. 3-7 in conjunction with FIGS. 1 and 2, a plurality of light-emitting diode elements or LEDs 34 are mounted upon and through the surface of the head portion 14 in separate linear arrays on opposite sides of the magnifying lens window 20 to direct illumination upon the viewing area and within the field of view observed through the window. Conventional in their semi-conductor construction and low current operation, the LEDs 34 are discrete elements commercially available in a variety of sizes and physical packages, those standard T1 (3 mm) and T-1¾ (5 mm) sizes in domed or cylindrical packages with flanges being generally preferred for the present invention. The LEDs 34 are preferably "white" in their light emissions to provide brighter illumination but alternate color emissions may be employed to provide sufficient light to illuminate the intended field of view. The number of LEDs 34 can vary in each array, typically there being two (2) to four (4), as shown, on either side of the magnifying lens window 20.

Figure 7:
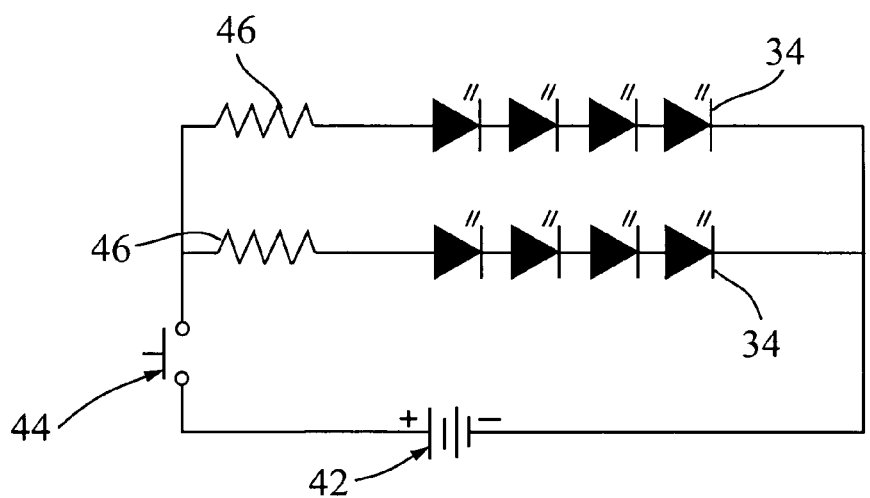
FIG. 7 is a schematic circuit diagram for the illumination means associated with the present insect locator and removal tool.

As best seen in FIG. 7, the LEDs 34 in the respective linear arrays are electrically connected in series and the respective series arrays are connected in parallel branches, each through a current limiting resistor 46. The voltage source providing power to drive the LEDs 34 and their light emissions is preferably a replaceable DC battery 42, typically a standard 9V or 12V alkaline battery being sufficient to power the LEDs in the circuit array described. Typically, the forward operating voltage of the LEDs is between about 1.5 and 3.5 volts, the higher range being characteristic of the "white" LEDs, while the forward operating current is about 20 mA or less. The value of the resistor 46 needed is determinable by known formulas based upon the voltage source, the operating specifications and number of LEDs 34 in the each array. In its drive circuit, the LEDs 34 are further controlled and turned "on" and "off" using a conventional push button electrical switch 44 connected between the battery 42 and the respective LED arrays, as shown in FIG. 7. The physical switch component 38 is mounted on the handle 16 in position for actuation by the user's thumb. Also provided on the handle 16 is a releasable compartment door 40 for access to and replacement of the battery 42 and a grip surface 36 intended for the fingers of the user in handling the present tool 10.

In the operational use of the present tool 10, the user will switch "on" the LEDs and holding the working side of the tool body 12 by its handle 16 with the head portion 14 and its respective sets of teeth 22 and 24 turned away from the user and directed toward the skin surface to be treated, the tool is stroked through the hair of the human or animal under treatment with the rake-like teeth set being gently pulled in the direction opposite of the natural growth of the hair. This gentle stroking movement of the rake-like teeth set 22 in advance and forwardly of the magnifying lens window 20 will provide a clear, illuminated and magnified view of the exposed skin area through the window as the hair is pulled back by the rake-like teeth. If an insect or foreign body is found and observed in an exposed area, the user, still holding the tool 10 by its handle 16, simply reverses the direction of the stroke and leading with the inclined comb-like set 24, moves back through the same area in the natural direction of the hair growth, to collect the insect within the closely spaced tines 24a and gently remove it from the area.

Figure 8:
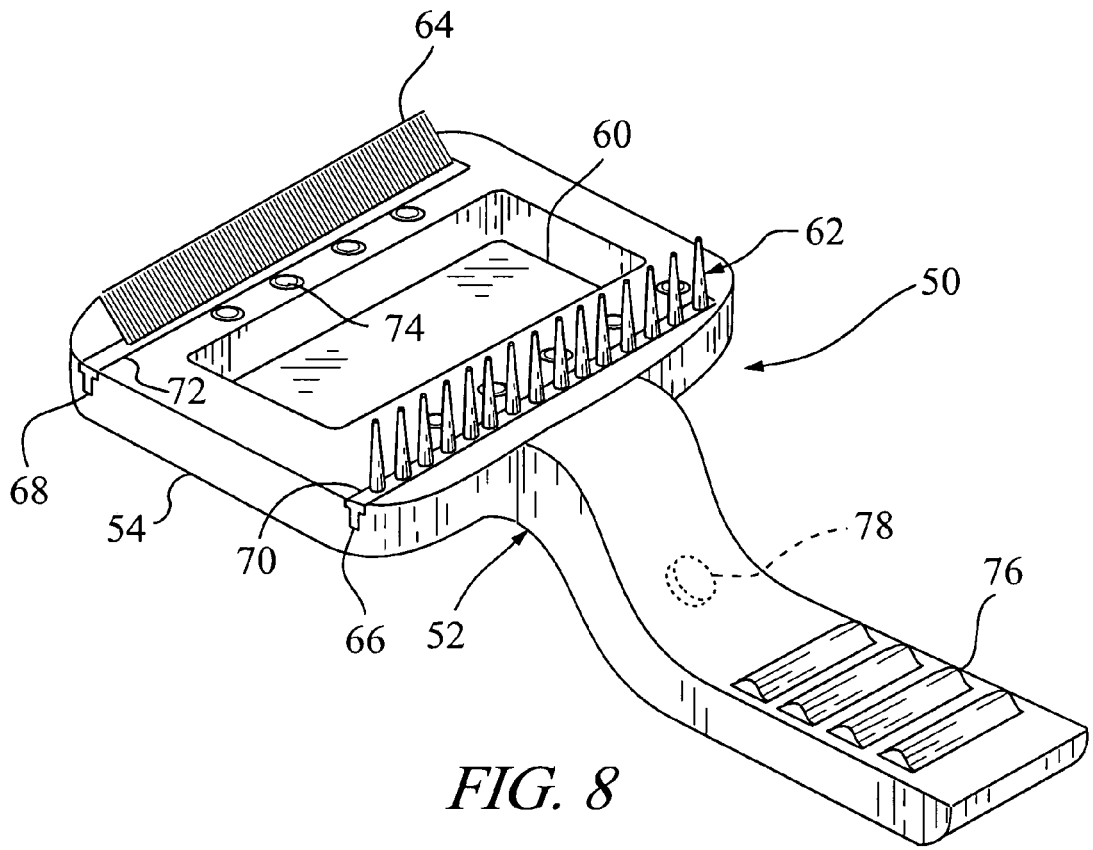
FIG. 8 is a perspective view of an alternate embodiment of the insect locator and removal tool made according to the present invention.

In FIG. 8, there is shown a modified physical embodiment of the present insect locator and removal tool, generally designated 50. In this modified embodiment of the present tool 50, the handle 56 on the tool body 52 is altered both in its construction and the position attached to the head portion 54 of the tool body so that the handle is upwardly inclined with respect to the head portion and disposed longitudinally in the same line of direction as the intended working movements of the rake-like teeth set 62 and comb-like teeth set 64. Different from handle 16 that is substantially level with head portion 14 and disposed longitudinally in a perpendicular direction to the working movements of the respective sets of rake-like teeth and comb-like teeth 22 and 24, the restructured and repositioned handle 56 allows the associated tool 50 and its respective rake-like teeth and comb-like teeth sets 62 and 64 to be moved through the hair in proper sequence and direction without need to turn the tool 50 around by the handle. Otherwise and in all other respects, the alternative tool 50 shown in FIG. 8 is the same as the preferred tool embodiment 10 described above and shown in the foregoing figures.

Therefore, it is apparent that the described invention provides an improved tool for both locating and removing parasitic insects, such as fleas, lice and ticks, and other foreign matter from the hair-covered skin of an affected host victim. More particularly, it is evident that the present invention provides a single hand-held tool capable of locating parasitic insects and other foreign matter upon areas of hair-covered skin with the further capability of removing the insects and other located matter in a systematic process using the single tool. In addition, the present invention provides an improved insect locator and removal tool that is easy to manipulate and safe to use on the skin surfaces of pet animals and humans alike. With its replaceable sets of teeth on the working side of the tool, the present invention can be easily altered and assembled with alternate sets of teeth to maximize performance based upon the quality, thickness and length of the hair covering the treated areas. This replaceable teeth feature also allows the present inventive tool to be more effectively cleaned and maintained for repeated and extended usage. Furthermore, the present inventive tool is lightweight yet sturdy in its construction, relatively inexpensive to fabricate and simple to assemble.

Obviously, other embodiments and modifications of the present invention will readily come to those or ordinary skill in the art having the benefit of the teachings presented in the foregoing description and drawings. Alternate embodiments of different shapes and sizes, as well as substitution of known materials or those materials that may be developed at a future time to perform the same function as the present described embodiment are therefore considered to be part of the present invention. Accordingly, it is understood that this invention is not limited to the particular embodiment described, but rather is intended to cover modifications within the spirit and scope of the present invention as expressed in the appended claims.

What is claimed is:

1. A tool for locating and removing an insect from an area of skin substantially covered by hair, comprising:
    a tool body including a head portion having a window opening incorporated therein and a handle member extending therefrom;
    lens means operatively connected to the head portion within the window opening for magnifying a viewing area therethrough;
    light-emitting means incorporated into said tool body for illuminating the magnified viewing area, said light-emitting means comprising a plurality of LEDs mounted upon the head portion in separate linear arrays on opposite sides of the window opening and electrical drive means operatively connected to said LEDs for controlling light emissions therefrom;
    an assembly of rake-like teeth releasably engaged to the head portion of said tool body, said assembly set of rake-like teeth being disposed along one side of the window opening with the rake-like teeth projecting substantially perpendicular thereto for exposing the skin area in the illuminated magnified viewing area as the teeth are moved through the hair thereby locating the insect; and
    an assembly of comb-like teeth separate and apart from said assembled set of rake-like teeth, said comb-like teeth set being releasably engaged to the head portion of said tool body and disposed along the opposite side of the window opening from said rake-like teeth set with the comb-like teeth inclined at an angle for removing the located insect from the skin area.

2. An insect locator and removal tool according to claim 1, wherein said lens means further comprises:
    a magnifying lens made to insert and mount in place within the window opening.

3. An insect locator and removal tool according to claim 2, wherein said magnifying lens is formed and adapted to releasably engage the window opening and re removed therefrom.

4. An insect locator and removal tool according to claim 3, wherein said magnifying lens has a magnification power in the range between 10×-30×.

5. An insect locator and removal tool according to claim 1, wherein said electrical drive means comprises:
    a DC voltage source;
    an electrical switch operatively connected between the DC voltage source and the linear arrays of said LEDs; and
    a current-limiting resistor operatively connected in line with each array of said LEDs.

6. An insect locator and removal tool according to claim 5, wherein the respective linear arrays of said LEDs are electrically connected in series and the respective series are connected in parallel branches.

7. An insect locator and removal tool according to claim 6, wherein the light emissions from said LEDs are white in color.

8. An insect locator and removal tool according to claim 1, wherein said assembly of rake-like teeth further comprises:
    a base strip adapted to engage the head portion and releasably connect thereto along one side of the window opening;
    a plurality of rake-like teeth arranged in parallel and attached to said base strip, said rake-like teeth being adapted in form and spacing to separate the hair covering the skin area when moved therethrough.

9. An insect locator and removal tool according to claim 1, wherein said assembly of comb-like teeth further comprises:
    a base strip adapted to engage the head portion and releasably connect thereto along one side of the window opening; and
    a plurality of fine teeth members connected to said base strip, said fine teeth members being narrow in form and closely spaced apart along the top of the base strip at an inclined angle to facilitate engagement and removal of an insect from the exposed area of skin.

10. An insect locator and removal tool according to claim 9, wherein the inclined angle of said fine teeth members is set at about 45°.

11. An insect locator and removal tool according to claim 1, wherein the head portion of said tool body is pad-like and substantially rectangular in form and made to extend from the handle member in substantially the same plane.

12. An insect locator and removal tool according to claim 11, wherein the window opening is substantially rectangular in its configuration and sized to maximize the field of view through the head portion.

13. A tool for locating and removing foreign matter from an area of skin substantially covered by hair, comprising:
 a tool body including a pad-like head portion substantially rectangular in form having a window opening incorporated therein and a handle member extending therefrom;
 an optical lens made to insert and mount in place within the window opening for magnifying a viewing area therethrough;
 a plurality of LEDs mounted upon the head portion in separate linear arrays on opposite sides of the window opening to direct illumination upon the magnified viewing area;
 a plurality of rake-like teeth members projecting perpendicularly from the head portion of said tool body along one side of the window opening, said plurality of rake-like teeth members being made in form and spacing to separate the hair covering the skin area when moved therethrough in a direction exposing the area of skin in the illuminated magnified viewing area; and
 a plurality of comb-like teeth members projecting at an inclined angle from the head portion of said tool body along the opposite side of the window opening, said plurality of comb-like teeth being made narrow in form and closely spaced apart to facilitate engagement and removal of the foreign matter from the exposed area of skin when moved therethrough in reverse direction from that movement of said rake-liketeeth members.

* * * * *